United States Patent
Van Holten et al.

(10) Patent No.: US 9,238,088 B2
(45) Date of Patent: Jan. 19, 2016

(54) SURGICAL BARRIERS HAVING ADHESION INHIBITING PROPERTIES

(71) Applicant: Ethicon, Inc., Somerville, NJ (US)

(72) Inventors: Robert W. Van Holten, Flemington, NJ (US); Jagdishchandra C. Patel, Lawrenceville, NJ (US)

(73) Assignee: Ethicon, Inc., Somerville, NJ (US)

( * ) Notice: Subject to any disclaimer, the term of this patent is extended or adjusted under 35 U.S.C. 154(b) by 9 days.

(21) Appl. No.: 14/093,797

(22) Filed: Dec. 2, 2013

(65) Prior Publication Data

US 2014/0093549 A1    Apr. 3, 2014

Related U.S. Application Data

(60) Division of application No. 12/338,349, filed on Dec. 18, 2008, now Pat. No. 8,629,314, which is a continuation-in-part of application No. 11/958,796, filed on Dec. 18, 2007, now Pat. No. 8,299,316.

(51) Int. Cl.
| | |
|---|---|
| *A61L 15/28* | (2006.01) |
| *A61L 31/10* | (2006.01) |
| *A61L 31/14* | (2006.01) |

(52) U.S. Cl.
CPC ............... *A61L 15/28* (2013.01); *A61L 31/10* (2013.01); *A61L 31/141* (2013.01); *Y10T 428/31986* (2013.01)

(58) Field of Classification Search
None
See application file for complete search history.

(56) References Cited

U.S. PATENT DOCUMENTS

| | | | |
|---|---|---|---|
| 3,364,200 A | | 1/1968 | Ashton et al. |
| 4,581,324 A | | 4/1986 | Wolff et al. |
| 4,626,253 A | | 12/1986 | Broadnax |
| 4,900,554 A | * | 2/1990 | Yanagibashi et al. ......... 424/448 |
| 5,002,551 A | | 3/1991 | Linsky et al. |
| 5,007,916 A | | 4/1991 | Linsky et al. |
| 5,180,398 A | | 1/1993 | Boardman et al. |
| 5,900,245 A | | 5/1999 | Sawhney et al. |
| 6,051,248 A | | 4/2000 | Sawhney et al. |
| 6,162,241 A | | 12/2000 | Coury et al. |
| 6,217,894 B1 | | 4/2001 | Sawhney et al. |
| 6,323,278 B2 | | 11/2001 | Rhee et al. |
| 6,352,710 B2 | | 3/2002 | Sawhney et al. |
| 6,410,645 B1 | | 6/2002 | Pathak et al. |
| 6,416,778 B1 | * | 7/2002 | Ragavan et al. .............. 424/430 |
| 6,458,889 B1 | | 10/2002 | Trollsas et al. |
| 6,495,127 B1 | | 12/2002 | Wallace et al. |
| 6,534,591 B2 | | 3/2003 | Rhee et al. |
| 6,541,460 B2 | | 4/2003 | Petito |
| 6,624,245 B2 | | 9/2003 | Wallace et al. |
| 6,652,874 B2 | * | 11/2003 | Ragavan et al. .............. 424/430 |
| 6,733,774 B2 | | 5/2004 | Stimmeder et al. |
| 6,762,336 B1 | | 7/2004 | MacPhee et al. |
| 6,833,408 B2 | | 12/2004 | Sehl et al. |
| 6,911,496 B2 | | 6/2005 | Rhee et al. |
| 6,969,400 B2 | | 11/2005 | Rhee et al. |
| 7,198,786 B2 | | 4/2007 | Redl et al. |
| 8,629,314 B2 | * | 1/2014 | Van Holten et al. ............ 602/48 |
| 2004/0214770 A1 | | 10/2004 | Reich et al. |
| 2004/0258723 A1 | * | 12/2004 | Singh et al. .................... 424/401 |
| 2005/0113849 A1 | * | 5/2005 | Popadiuk et al. .............. 606/151 |
| 2005/0226916 A1 | | 10/2005 | Cochrum et al. |
| 2006/0051340 A1 | | 3/2006 | Uchida et al. |
| 2006/0147492 A1 | | 7/2006 | Hunter et al. |
| 2006/0240064 A9 | | 10/2006 | Hunter et al. |
| 2006/0258995 A1 | | 11/2006 | Pendharkar et al. |
| 2008/0071300 A1 | * | 3/2008 | Popadiuk et al. .............. 606/151 |
| 2008/0206293 A1 | * | 8/2008 | Toreki et al. .................. 424/404 |

FOREIGN PATENT DOCUMENTS

| | | |
|---|---|---|
| EP | 0142086 | 5/1985 |
| EP | 0275550 | 7/1988 |
| EP | 0815881 | 7/1998 |
| EP | 1341561 | 2/2007 |
| GB | 293655 | 4/2004 |
| WO | WO 03/026544 | 4/2003 |
| WO | WO 2004/024195 | 3/2004 |
| WO | WO 2004/028547 | 4/2004 |
| WO | WO 2004/064878 | 8/2004 |
| WO | WO 2007/117237 | 10/2007 |

OTHER PUBLICATIONS

International Search Report PCT/US2008/087493 dated Mar. 22, 2010.
International Search Report PCT/US2008/087500 dated Apr. 15, 2010.
Encyclopedia of Polymer Science and Engineering, "Molecular Weight Determination to Pentadiene Polymers", vol. 10, pp. 204-253 (1987).
N. Zaji, "Laparoscopic Repair of Perforated Peptic Ulcers Versus convention Open Surgery", Laparoscopic Hospital, New Delhi, India, Jul. 2007.
Graham, D.Y., "Treatment of Peptic Ulcers Caused by Helicobacter Pylori", 328 N. England Journal Medicine, pp. 349-350, (1993).
Donovan, A.J., "Perforated Duodenal Ulcer an Alternative Therapeutic Plan", 133 Arch Surg., pp. 1166-1171 ( Nov. 1998).
Vandamme, T., "The Use of Polysaccharides to Target Drugs to the Colon", 48 Car Poly, pp. 219-231 (2002).
Lieberman, et al., Pharmaceutical Dosage Forms: Tablets vol. 3, Chapters 2, 3, and 4 (1982).

* cited by examiner

*Primary Examiner* — Peter A Salamon
(74) *Attorney, Agent, or Firm* — David R. Crichton

(57) ABSTRACT

An adhesion inhibiting surgical barrier. The surgical barrier includes a wound-facing polymeric coating comprising an enteric polymer; and at least one flexible substrate, the at least one flexible substrate having at least one exterior surface, wherein the polymeric coating is applied to the at least one flexible substrate to substantially cover the at least one exterior surface thereof. A method of inhibiting the formation of adhesions in a patient who has undergone a surgical procedure and a method of repairing a gastric or duodenal perforation are also described herein.

5 Claims, No Drawings

SURGICAL BARRIERS HAVING ADHESION INHIBITING PROPERTIES

CROSS REFERENCE TO RELATED APPLICATIONS

This application is a divisional of pending continuation-in-part U.S. application Ser. No. 12/338,349 filed Dec. 18, 2008, claiming priority to U.S. Pat. No. 8,299,316 issued Oct. 30, 2012, the entire disclosures of which are hereby incorporated in their entirety.

FIELD

Disclosed herein are adhesion inhibiting barriers and methods for their production and use.

BACKGROUND

Adhesion formation is a well-known complication of many types of surgical procedures, particularly abdominal and bowel surgeries. Adhesion formation typically occurs as a result of the formation of a fibrin clot, which transforms into scar tissue connecting different tissues that are normally separated. Surgical intervention is frequently required in order to eliminate the adhesions, although the adhesions can, and often do, reappear following the surgery. The primary objective of adhesion inhibiting barriers is to interrupt the adhesion formation mechanism, which is believed to result from the diffusion of fibrinogen into the space between the tissues subject to surgical trauma, thereby causing the formation of fibrin clots in the space.

As such, post-surgical adhesions present a major healthcare problem of significant clinical and medical economic relevance. Abdominal adhesions are not only the leading cause of small bowel obstruction, but also major sources of infertility and of abdominal and pelvic pain. It has been shown that post-surgical adhesions cause at least about 20% of cases of infertility and about 40% of cases of chronic pelvic pain.

Although it is known that the incidence of post-surgical adhesions may be reduced by various improvements in surgical techniques and/or better instrumentation, adhesions cannot be prevented without adjuvant therapy, because every minute trauma may induce their formation. In view thereof, significant efforts have been made to provide effective means and treatment methods for reducing or preventing such adhesions connected with surgery. Many substances or constructs have been reported to have positive effects on surgical adhesions, such as collagen films, collagen gels, and sodium hyaluronate/carboxymethylcellulose film and fibrin glue.

In addition to acting as an adhesion barrier, a successful anti-adhesion formulation should be "biocompatible," meaning that it has minimal to no medically unacceptable toxic or injurious effect on the biological function of the subject, and "bioabsorbable," meaning that it can be absorbed by the tissue without a significant amount remaining in the subject as an implant device. It is to be understood that such bioabsorbable materials are broken down by the body, then the resulting products are excreted therefrom by various means, including passage in urine, feces or as carbon dioxide in the breath. Thus, the formulation should remain in the body for a sufficient period of time to be effective in separating the tissue and preventing adhesions, while being absorbed by the tissue once the danger of adhesion formation has ended, thereby minimizing any long term effects which may result from the use of an implant device.

Perforation is the second most common complication of peptic ulcer and is often associated with NSAID use especially in the elderly population. See N Zaji, "Laparoscopic Repair of Perforated Peptic Ulcers Versus Conventional Open Surgery," Laparoscopic Hospital, New Delhi, India, July 2007. Approximately 10-20% of patients with peptic ulcers suffer perforation of the stomach or duodenum, in which a chemical peritonitis develops initially from the gastric and duodenal secretion then bacterial contamination superimposed within hours. *Helicobacter pylori* infection plays a central role in the genesis of peptic ulcer. See Graham, D. Y., "Treatment of peptic ulcers caused by *Helicobacter pylori*," 328 N Engl J Med 349-350 (1993).

The perforation of a duodenal ulcer allows for the egress of gastric and duodenal contents into the peritoneal cavity with a resulting initial chemical peritonitis. If there is continued leakage of gastro-duodenal contents, bacterial contamination of the peritoneal cavity could occur. See A. J. Donovan, "Perforated Duodenal Ulcer An Alternative Therapeutic Plan." 133 ARCH SURG 1166-1171, (November 1998).

U.S. Pat. No. 7,198,786 proposes a method of reducing or preventing adhesions which would form in a patient during or after surgery by administering to the wound surface of a patient a fibrinogen solution in an amount of about 0.025 ml fibrinogen/$cm^2$ to about 0.25 ml fibrinogen/$cm^2$ of the surface being at risk for developing adhesions. The use of fibrinogen in a preparation comprising fibrinogen at a concentration of 20 to 80 mg/ml for the reduction or prevention of post-surgical adhesion formation is also proposed.

EP 1,341,561 proposes a layered wound dressing material comprising: a wound facing hydrogel layer and a barrier layer, wherein the barrier layer comprises a pH-sensitive material that is substantially insoluble in water at 25° C. under acidic conditions, but substantially soluble in water at 25° C. under neutral or alkaline conditions. In use, the hydrogel layer absorbs and is gradually neutralized by wound exudate until its pH rises to a level that causes dissolution of the barrier layer, thereby allowing excess exudate to flow out from the hydrogen layer. Also proposed are wound dressings comprising barrier layers and methods of use of such dressings.

Despite these advances in the art, it would be desirable to provide a suitable adhesion inhibiting barrier as well as a method for reducing or preventing post-surgical adhesions in a patient. There also remains a need for a barrier for containing the gastric and duodenal contents of a perforated ulcer in order to minimize the risk of further deterioration of the compromised area.

SUMMARY

Disclosed herein are surgical barriers. In one form, the surgical barrier includes a wound-facing polymeric coating comprising, consisting of, and/or consisting essentially of an enteric polymer, an optional non-enteric polymer and an optional plasticizer; and at least one flexible substrate, the at least one flexible substrate having at least one exterior surface, wherein the polymeric coating is applied to the at least one flexible substrate to substantially cover the at least one exterior surface thereof.

In one aspect, the enteric polymer may be selected from hydroxypropyl methylcellulose phthalate; hydroxypropyl methylcellulose acetate succinate; enteric acetate derivatives; dimethylcellulose acetate; enteric acrylate derivatives; and derivatives, salts, copolymers, and combinations thereof.

In another aspect, the enteric acetate derivative is selected from polyvinylacetate phthalate, cellulose acetate butyrate, cellulose acetate trimellitate, cellulose acetate propionate and cellulose acetate phthalate.

In yet another aspect, the enteric acrylate derivative may include a polymethacrylate-based polymer selected from (poly-(methacrylic acid) poly(methyl methacrylate) in a ratio of 1:2; and poly(methacrylic acid) poly(methyl methacrylate) in a ratio of 1:1.

In still yet another aspect, the enteric polymer and the optional non-enteric polymer may be present in the polymeric coating in an amount of about 60:40 to about 40:60 by weight.

In a further aspect, the polymeric coating may contain, based upon the total weight of the polymeric coating, from about 30 to about 60 percent of the enteric polymer; from about 30 percent to about 60 percent of the non-enteric polymer; and from about 0 percent to about 40 percent of the plasticizer.

In a still further aspect, the at least one substrate, which in some forms may be a flexible substrate, may be configured in a planar form, straw-like form, cylindrical form, fibrillar form, filament-like form, or spherical form and may include a plurality of individual substrates.

In a yet still further aspect, the at least one flexible substrate may be selected from film, nonwoven fabric, or woven fabric and is comprised of collagen, oxidized polysaccharides, aliphatic polyester polymers and/or copolymers of one or more monomers selected from the group consisting of D-lactic acid, L-lactic acid, lactide (including L-, D-, meso forms), glycolic acid, glycolide, ε-caprolactone, p-dioxanone, and trimethylene carbonate, and derivatives, salts, and combinations thereof.

In one aspect, the at least one flexible substrate is comprised of oxidized regenerated cellulose.

In another aspect, the surgical barrier may have incorporated in or adhered to the polymeric coating a substance selected from blood coagulation factors, stabilizers, fibrinolysis inhibitors, biologic active substances including antibiotics, chemotherapeutics, fibroblastic growth factors, cell growth factors and combinations thereof.

In yet another aspect, the polymeric coating may be applied to the at least one flexible substrate by spraying, dipping, or enrobing to encapsulate the at least one flexible substrate.

In still yet another aspect, the polymeric coating may be applied to the at least one flexible substrate by lamination or coextrusion.

In a further aspect, the non-enteric polymer is selected from hydroxypropylcellulose, methylcellulose, hydroxypropylmethylcellulose, hydroxyethylmethylcellulose, hydroxyethylcellulose, hydroxyethylethylcellulose, cellulose acetate, carboxymethyl cellulose sodium, cellulose butyrate, acetaldehyde dimethylcellulose acetate and derivatives, salts, copolymers and combinations thereof.

In a still further aspect, the polymeric coating comprises a cellulose acetate phthalate and hydroxypropylcellulose, and said at least one flexible substrate comprises oxidized regenerated cellulose.

In another form, provided is a method of inhibiting the formation of adhesions in a patient having undergone a surgical procedure. The method comprises, consists of, and/or consists essentially of applying an adhesion inhibiting barrier to an area rendered susceptible to forming adhesions, the adhesion inhibiting barrier surgical barrier including a wound-facing polymeric coating comprising, consisting of, and/or consisting essentially of an enteric polymer, an optional non-enteric polymer and an optional plasticizer; and at least one flexible substrate, the at least one flexible substrate having at least one exterior surface, wherein the polymeric coating is applied to the at least one flexible substrate to substantially cover the at least one exterior surface thereof.

In yet another form, provided is a method of repairing perforations, such as gastric, duodenal, or other perforations existing in an acidic area, the method comprising, consisting of, and/or consisting essentially of: closing the perforation with a surgical barrier in the form of a patch, the surgical barrier comprising, consisting of, and/or consisting essentially of: i) a polymeric coating comprising an enteric polymer, an optional non-enteric polymer and an optional plasticizer; and ii) at least one flexible substrate, the at least one flexible substrate having at least one exterior surface, wherein the polymeric coating is applied to the at least one flexible substrate to substantially cover the at least one exterior surface thereof.

DETAILED DESCRIPTION

As used herein, "substantially covered" shall mean that greater than about 50%, that is, for example, greater than about 60%, greater than about 70%, greater than about 80%, greater than about 90%, greater than about 95%, greater than about 97%, or greater than about 99% percent of an exterior surface area is covered.

As used herein, "enteric" shall mean being able to be dissolved at a pH greater than that of the stomach (about 1.5 to about 3.0 pH), that is, for example, at a pH of greater than about 3.0 or greater than about 5.0 or greater than about 5.5 or greater than about 6.0 or that which is found in the intestines, that is, for example, greater than about 7.0, or that which is found in the small intestine duodenum, that is, for example, about 5.0 to about 6.0 pH, or that which is found in the large intestine Cecum and colon, that is, for example, about 5.5 to about 7.0 pH. See Vandamme, T., "The Use of Polysaccharides to Target Drugs to the Colon," 48 Car Poly 219-231 (2002).

Disclosed herein are adhesion inhibiting surgical barriers. In one form, the surgical barrier includes a polymeric coating comprising an enteric polymer, an optional non-enteric polymer and an optional plasticizer; and at least one substrate, which may be a flexible substrate, the at least one substrate having at least one exterior surface, wherein the polymeric coating is applied to the at least one flexible substrate to substantially cover the at least one exterior surface thereof. The polymeric coating, which faces the wound, serves as an adhesion-inhibiting layer.

Examples of suitable enteric components include, but are not limited to, hydroxypropyl methylcellulose phthalate; hydroxypropyl methylcellulose acetate succinate; enteric acetate derivatives including, but not limited to, polyvinylacetate phthalate, cellulose acetate phthalate ("CAP"), cellulose acetate propionate, cellulose acetate butyrate, cellulose acetate trimellitate; and enteric acrylate derivatives including, but not limited to, polymethacrylate-based polymers such as poly(methacrylic acid) poly(methyl methacrylate) in a ratio of 1:2 (commercially available from Rohm Pharma GmbH under the trademark Eudragit® S 100, Eudragit® L1000, Eudragit® L-300, Eudragit® FS30D, and Eudragit® L 100-55) and poly(methacrylic acid-) poly(methyl methacrylate) in a ratio of 1:1 (commercially available from Rohm Pharma GmbH under the trademark, Eudragit® L), and derivatives, salts, copolymers, and combinations thereof.

In forms where it is desired to have increased flexibility of the surgical barrier device, a plasticizer may be added to the polymeric coating in an amount, based upon the total weight of the polymeric coatings, from about 1 percent to about 35 percent. Example of suitable plasticizers include, but are not limited to, polyethylene glycol; propylene glycol; glycerin; sorbitol; triethyl citrate; tributyl citrate; dibutyl sebecate; diethylphthalate, dimethyl phthalate triacetin, glyceryl triacetate, tripropionin, glycerin vegetable oils, such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltri-n-butyl citrate; triethyl citrate, acetyltriethyl citrate, tri-n-butyl citrate, diethylmalate; diethyl fumarate; diethylmalonate; dioctylphthalate; dibutylsuccinate; glyceroltributyrate; glycerol monostearate; hydrogenated castor oil; substituted triglycerides and glycerides; and mixtures thereof.

Optionally, the polymeric coating may also comprise additional, non-enteric components including, but not limited to, hydroxypropylcellulose ("HPC"), methylcellulose ("MC"), hydroxypropylmethylcellulose ("HPMC"), hydroxyethylmethylcellulose ("HEMC"), hydroxyethylcellulose ("HEC") hydroxyethylethylcellulose ("HEEC"), cellulose acetate, carboxymethyl cellulose sodium, cellulose butyrate, acetaldehyde dimethylcellulose acetate, and derivatives, salts, copolymers and combinations thereof.

In one form, the adhesion inhibiting polymeric coating includes a blend of cellulose acetate phthalate and HPC.

In one form, the weight ratio of the enteric component and the non-enteric component in the polymeric coating may range from about 60:40 to about 40:60, or about 50:50.

In another form, the adhesion inhibiting polymeric coating may be comprised of, based upon the total dry weight of the adhesion inhibiting polymeric coating, from about 30 to about 60 percent or from about 40 percent to about 50 percent of enteric component; from about 30 percent to about 60 percent or from about 40 percent to about 50 percent of a non-enteric cellulosic component; and from about 0 percent to about 40 percent or from about 1 percent to about 35 percent of plasticizer.

In one form, wherein HPC is incorporated in the polymeric coating, the average molecular weight of the HPC may be greater than about 140,000, or greater than or equal to about 360,000 or greater than or equal to about 370,000.

The polymeric coating can also be used as a carrier for active components known in the art, which include but are not limited to hemostatic agents, tissue healing factors and antibacterial material. Examples of such known active components, which include but are not limited to blood coagulation factors; stabilizers; fibrinolysis inhibitors; biologic active substances, including antibiotics, chemotherapeutics, fibroblastic growth factors, and cell growth factors; and combinations thereof may be dispersed within the polymeric coating or applied to the face of the polymeric coating. Active components contemplated herein further include those selected from the group consisting of albumin, ancrod, batroxobin, ecarin, elastin, epinephrine, Factor X/Xa, Factor VII/VIIa, Factor IX/IXa, Factor XI/XIa, Factor XII/XIIa, calcium chloride fibrin, ficolin, fibronectin, gelatin, globin, haptoglobin, hemoglobin, heparinase, inhibin, insulin, interleukin, lamininthrombin, platelet surface glycoproteins, prothrombin, selectin, transferin, von Willebrand Factor, vasopressin, vasopressin analogs, procoagulant venom, platelet activating agents and synthetic peptides having hemostatic activity. One or more of these active components may be used in combination, as those skilled in the art will plainly understand.

The at least one substrate suitable for use in the surgical barrier device disclosed herein may be in any shape or size that may suitably be substantially covered by the polymeric coating. For example, the substrate may be planar, straw-like, cylindrical, fibrillar, filament-like, or spherical in shape. The at least one substrate may be comprised of a plurality of the substrates, which may be the same or differ with respect to composition, thickness, etc., as those skilled in the art will plainly understand.

In one form, the at least one substrate, which may be a flexible substrate, includes a first exterior surface having a first polymeric coating thereon and a second exterior surface having an optional second polymeric coating thereon. In another form, incorporated in or adhered to the first polymeric coating is a first substance selected from blood coagulation factors, stabilizers, fibrinolysis inhibitors, biologic active substances including antibiotics, chemotherapeutics, fibroblastic growth factors, cell growth factors and combinations thereof, and incorporated in or adhered to the second polymeric coating is a second substance selected from blood coagulation factors, stabilizers, fibrinolysis inhibitors, biologic active substances including antibiotics, chemotherapeutics, fibroblastic growth factors, cell growth factors and combinations thereof, wherein the first substance is independent of the second substance. In one form, the first polymeric coating and the second polymeric coating are comprised of cellulose acetate phthalate and the at least one flexible substrate is comprised of oxidized regenerated cellulose. In one form, the polymeric coatings may be applied to the at least one substrate by spraying, dipping, enrobing, lamination, or coextrusion to encapsulate the at least one substrate. As may be appreciated, the first and second polymeric coatings may differ with respect to composition, concentration, thickness, method of application, pH sensitivity, molecular weight, etc., as those skilled in the art will plainly understand.

In one form, planar substrates may in the form of a film or a fabric. Examples of fabrics include, but are not limited to, a nonwoven, a woven, a knit, a matte, a batt, or a crimp. As may be appreciated, the polymeric coating shields at least one surface of the at least one substrate from acidic moieties that may be present in the substrate, for example in the case where carboxylic-oxidized cellulose is used as the fabric.

The substrate may be comprised of components selected from collagen, oxidized polysaccharides, aliphatic polyester polymers and/or copolymers of one or more monomers selected from the group consisting of D-lactic acid, L-lactic acid, lactide (including L-, D-, meso forms), glycolic acid, glycolide, ε-caprolactone, p-dioxanone, and trimethylene carbonate, and mixtures or blends thereof.

In one form, the substrate may be comprised of oxidized polysaccharides, in particular oxidized cellulose and the neutralized derivatives thereof. For example, the cellulose may be carboxylic-oxidized or aldehyde-oxidized cellulose. In one form, oxidized regenerated polysaccharides including, but without limitation, oxidized regenerated cellulose may be used to prepare the second absorbable woven or knitted fabric. Regenerated cellulose possesses a higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of which are hereby incorporated by reference as if set forth in its entirety. Examples of fabrics that may be utilized include, but are not limited to, Interceed® absorbable adhesion barrier, Surgicel® absorbable hemostat; Surgicel Nu-Knit® absorbable hemostat; and Surgicel® Fibrillar absorbable hemostat; each available from Johnson & Johnson Wound Management Worldwide or Gynecare Worldwide, each a division of Ethicon, Inc., Somerville, N.J. U.S. Pat. No. 5,007,916 discloses the aforementioned Interceed® absorbable adhesion barrier and methods for making same, the contents of which are hereby incorporated by reference for all that they disclose.

The substrate may alternatively, or additionally, be comprised of a film or fabric of aliphatic polyester polymers, copolymers, or blends thereof. The aliphatic polyesters are typically synthesized in a ring opening polymerization of monomers including, but not limited to, lactide (including L-, and D-, meso forms), glycolic acid, glycolide, ε-caprolactone, p-dioxanone (1,4-dioxan-2-one), and trimethylene carbonate (1,3-dioxan-2-one). The aliphatic polyesters, in some cases, can be made by polycondensation of for instance, D-lactic acid, L-lactic acid and/or glycolic acid. In one form, the fabric comprises a copolymer of glycolide and lactide, in an amount ranging from about 70 to 95% by molar basis of glycolide and the remainder lactide.

The substrate may also comprise an oxidized regenerated cellulose/polypropylene/polydiaxanone (PDS) mesh, commercially available from Ethicon, Inc. under the tradename, Proceed®. U.S. Patent Publication Nos. 2005/0113849A1 and 2008/0071300A1 disclose the aforementioned Proceed® oxidized regenerated cellulose/polypropylene/PDS mesh substrate and methods for making same, the contents of which are hereby incorporated by reference for all that they disclose. In one form, both exterior surfaces of the oxidized regenerated cellulose/polypropylene/PDS mesh may be substantially coated with the polymeric coating, and in another form only one exterior surface of this substrate may be substantially coated with the polymeric coating.

The film or fabric used to form the substrate may be comprised of aliphatic polyester polymers, copolymers, or blends thereof alone or in combination with oxidized polysaccharide fibers.

In one form, the substrate may be comprised of one or more layers, wherein at least one layer is comprised of the aforementioned components suitable for the substrate layer.

The thickness of the at least one substrate may vary depending upon, for example, the non woven technique used, the coating technique used, etc., but typically may range from about 200 µm to about 600 µm or about 250 µm to about 550 µm.

The surgical barrier may be comprised of, based upon the total weight of the barrier, from about 65 percent to about 10 percent, e.g., from about 50 percent to about 30 percent of the polymeric coating and from about 35 percent to about 90 percent, e.g., from about 50 percent to about 70 percent of the substrate.

When a fabric is used to form the substrate of the adhesion inhibiting barriers disclosed herein, the fabric may be made weaving, knitting, matteing, spunlaid (meltblown, flashspun, spunbounding), wetlaid, drylaid or short fiber airlaid or known methods for making nonwovens. The fabric utilized in the present invention may be woven or knitted, for example, as described in U.S. Pat. Nos. 4,626,253, 5,002,551 and 5,007,916, the contents of which are hereby incorporated by reference herein as if set forth in its entirety.

The fabric utilized in the present invention may be nonwoven, for example, as described in U.S. Patent Publication No. 2006/0258995 A1, the contents of which are hereby incorporated by reference herein in their entirety.

In another form, disclosed herein is a method of inhibiting, i.e., reducing or preventing, the formation of adhesions in a patient having undergone a surgical procedure. The method includes the step of applying an adhesion inhibiting barrier to an area rendered susceptible to forming adhesions, the adhesion inhibiting surgical barrier including a wound-facing polymeric coating comprising an enteric polymer, an optional non-enteric polymer and an optional plasticizer; and at least one flexible substrate, the at least one flexible substrate having at least one exterior surface, wherein the polymeric coating is applied to the at least one flexible substrate to substantially cover the at least one exterior surface thereof.

Surgeons frequently have a need to inspect sites for hemostasis without disturbing the wound site. In forms wherein the barrier is comprised of, for example, an ORC substrate with at least one layer of cellulose acetate phthalate that is translucent in nature, inspection of the trauma site beneficially can be enabled.

Experience has shown that an adhesion barrier should not dissolve in the first few days, but should rather stay on the organ being treated for at least three or more days. We have unexpectedly found that that by applying a polymeric coating of the types disclosed herein onto a substrate, such as oxidized regenerated cellulose (ORC), the polymeric coating is preserved for about 6 to about 10 days, depending on the environmental conditions. Beneficially, this allows the substrate employed to remain intact.

As those skilled in the art plainly recognize, an adhesion barrier should stay in place to be efficacious. We have also unexpectedly found that the resultant surgical barrier disclosed herein provides a higher propensity to stay in place relative to an enteric film alone.

In addition, we have also unexpectedly found that the resultant adhesion barrier possesses improved handling characteristics. As may be appreciated, surgeons desire a barrier that retains its structure during application, so that it can be easily placed in the affected area. It has been observed that, for example, an ORC matrix typically becomes a limp gelatinous material in less than about one minute when exposed to body fluids. By contrast, the barriers disclosed herein possess improved handling characteristics over such matrices alone.

Currently, many mesh-type materials are not recommended for use in a bloody field due to concern that, when wetted with blood, the mesh may serve to induce adhesion formation rather than reduce their occurrence. We have also unexpectedly found that the adhesion inhibiting barriers disclosed herein can be immersed in a pool of blood without inducing adhesion formation.

The adhesion inhibiting barriers disclosed herein are also suitable for treating ulcerated areas of the digestive tract. As such, the barrier may be applied directly to the desired surface location of the ulcerated area such that the polymeric coating faces the ulcerated area.

As those skilled in the art recognize, a portion of patients with peptic ulcers suffer perforation of the stomach or duodenum, in which a chemical peritonitis develops initially from the gastric and duodenal secretion, followed by bacterial contamination.

As indicated above, the surgical barriers disclosed herein are suitable in repairing gastric or duodenal perforations. In accordance herewith, in one form, provided is a method of repairing a gastric or duodenal perforation, the method comprising closing the perforation with a surgical barrier in the form of a patch, the surgical barrier comprising: i) a polymeric coating comprising an enteric polymer, an optional non-enteric polymer and an optional plasticizer; and ii) at least one flexible substrate, the at least one flexible substrate having at least one exterior surface, wherein the polymeric coating is applied to the at least one flexible substrate to substantially cover the at least one exterior surface thereof.

In yet another form, disclosed herein is a method of making an adhesion inhibiting surgical barrier, the surgical barrier comprising: i) a wound-facing polymeric coating comprising an enteric polymer, an optional non-enteric polymer and an optional plasticizer; and ii) at least one flexible substrate, the at least one flexible substrate having at least one exterior surface, wherein the polymeric coating is applied to the at least one flexible substrate to substantially cover the at least one exterior surface thereof.

In one form wherein the substrate is planar, the substrate is substantially covered on one or both of its planar exterior surfaces with the polymeric coating. Alternatively, the substrate may be encapsulated with the polymeric coating. We have unexpected found that substrates, such as the fabrics of the types described herein, covered with polymeric coatings containing cellulose acetate phthalate and hydroxypropylcellulose have been found to significantly reduce or prevent the formation of adhesions in a rabbit sidewall model.

The polymeric coating can be applied to the substrate by a number of techniques or a combination of techniques. In one form, prior to the formation of the polymeric coating, the wound-facing polymeric coating formulation is liquid in nature, allowing the substrate to be coated with the polymeric coating by spraying, dipping, brushing or pouring the polymeric coating onto the surface of the substrate. As the organic solvent evaporates the formulation transforms from a gel consistency to a film. In an alternative form, the polymeric coating is applied to the substrate as a gel, or with greater organic solvent evaporation, as a paste. In yet another form, the polymeric coating is applied to the substrate in the form of a film via, for example, lamination, encasing, injection molding, and the like. In yet another form, the polymeric coatings may be applied to the substrate via any other suitable method known in the art. Suitable coating methods include high sheer granulation, fluid bed granulation, e.g. rotor granulation, fluid bed coating, wurster coating, coaccervation, spray drying, spray congealing, and the like and are described in, for example, Pharmaceutical Dosage Forms: Tablets Volume 3, edited by Herbert A. Lieberman and Leon Lachman, Chapters 2, 3, and 4 (1982).

The weight gain of the substrate after the addition of the polymeric coating thereto is, based upon the dry weight of the substrate alone, from about 10 percent to about 150 percent, e.g., from about 20 percent to about 130 percent or from about 30 percent to about 100 percent, from about 40 to about 80 percent.

Specific forms of the present invention will now be described further, by way of example. While the following examples demonstrate certain forms of the invention, they are not to be interpreted as limiting the scope of the invention, but rather as contributing to a complete description of the invention.

EXAMPLE 1

Manufacture of CAP Polymeric Coating Formulation

Into a test tube were added 0.8 grams of cellulose acetate phthalate (CAP), 0.8 grams of hydroxylpropyl cellulose (HPC) having a molecular weight of 370,000, 0.4 grams of glycerol, 164 ml of acetone and 24 ml of ethanol under ambient conditions and vortexed at about 3000 rpm for approximately 5 minutes until the mixture was homogeneous and had a viscosity of about 156 cP.

EXAMPLE 2

Manufacture of Substrate

A 2 cm×4.5 cm piece of a multilayered oxidized regenerated cellulose/polypropylene/polydiaxanone (PDS) mesh substrate, which is commercially available from Ethicon, Inc. under the tradename, "PROCEED," was immersed in a mixture containing 16 ml of acetone and 24 ml of ethanol under ambient conditions and vortexed at about 3000 rpm for approximately 5 minutes. The resulting substrate was then air-dried under ambient conditions. U.S. Patent Publication Nos. 2005/0113849A1 and 2008/0071300A1 disclose methods for making oxidized regenerated cellulose/polypropylene/PDS mesh substrate, the contents of which are hereby incorporated by reference for such details.

This procedure was repeated for 19 additional pieces of such substrate.

EXAMPLE 3

Coating Substrate with Polymeric Coating

A piece of the substrate, prepared in accordance with Example 2, was coated with the polymeric coating of Example 1 by immersing the substrate in the polymeric coating mixture under ambient conditions. The polymeric coating mixture was spread over the surface of the resulting substrate with a blade. The resulting dry weight gain of polymeric coating material on the substrate was, relative to the coated substrate alone, about 50 percent.

This procedure was repeated with 19 additional pieces of the substrate from Example 2.

EXAMPLE 4

Adhesion Model Study Results

A 14-day adhesion evaluation study of prototypes in the rabbit sidewall model was conducted to assess the extent and severity of adhesion formation of prototypes when compared to a control. A determination of the overall performance of each investigational test article was based on a comparison to the control with respect to the extent of adhesion formation and the severity of adhesion formation.

A test material is considered to be successful when it is shown to be superior to that of the negative control article, which, in this study, was the use of a suture alone.

Surgical Procedures

An approximate 12-cm incision was made along the midline of the ventral abdomen, approximately 4 cm caudal to the xiphoid process. The cecum was exteriorized and abraded by wiping the entire surface with a sterile dry gauze sponge until punctuate bleeding was achieved. A defect on each peritoneum abdominal sidewall, approximately 2×4.5 cm, was made lateral and parallel to the incision using sharp dissection. A window of peritoneum 2×4.5 cm was excised. The muscular layer below the excised peritoneum was abraded by wiping the entire surface with a sterile dry gauze sponge until punctuate bleeding was achieved. The defect was made approximately 2 cm lateral to the incision, and 3 cm caudal to the xiphoid process.

In the control group, the periphery of the defect area was sutured using PROLENE® polypropylene (4-0) suture in a continuous pattern. In the test article group, a rectangular piece of the test article, approximately 2×4.5 cm was sutured over the defect area using a PROLENE® suture (4-0) in a continuous pattern. The abdominal wall midline incision was closed with a simple continuous suture pattern over-sewn by several simple interrupted stitches using coated 3-0 VICRYL® (Polyglactin 910) suture. Subcutaneous tissues were closed with a simple continuous suture pattern using the same suture type. The skin was closed with Monocryl 3-0 suture and DERMABOND® HV Topical skin adhesive.

Adhesion Extent Score

Estimation of extent of adhesions to mesh surface
   0=no adhesions
   1=1-25%
   2=26-50%
   3=51-75%
   4=76-100%

Severity Score

Severity of most significant adhesions
   0=no adhesions
   1=adhesion separated with minimal effort
   2=adhesion separated with moderate effort
   3=adhesion separated with difficulty Results are presented in Table 1, wherein each line represents a test preformed with a test article on a single independent animal.

TABLE 1

14 Day Necropsy Scores

| Test Article | Right Side Extent | Right Side Severty | Left Side Extent | Left Side Severity | Total Score |
|---|---|---|---|---|---|
| Negative Control 4-0 | 3 | 3 | 4 | 3 | 13 |
| Suture Around | 4 | 2 | 4 | 1 | 11 |
| Periphery of Defect | 4 | 2 | 4 | 2 | 12 |
|  | 4 | 2 | 4 | 2 | 12 |
| Average total Score |  |  |  |  | 12.0 |
| ORC/Polypropylene/PDS | 2 | 2 | 1 | 1 | 6 |
| Mesh of Example 2 | 1 | 1 | 0 | 0 | 2 |
| Sutured Over Defect | 4 | 2 | 1 | 1 | 8 |
|  | 0 | 0 | 0 | 0 | 0 |
| Average Total Score |  |  |  |  | 4.0 |
| ORC/Polypropylene/PDS | 1 | 1 | 0 | 0 | 2 |
| CAP Coated Mesh of | 0 | 0 | 0 | 0 | 0 |
| Example 3 Sutured | 0 | 0 | 0 | 0 | 0 |
| Over Defect | 0 | 0 | 0 | 0 | 0 |
| Average Total Score |  |  |  |  | 0.5 |
| Hyaluronic Acid/CMC | 3 | 1 | 0 | 0 | 4 |
| Film[1] Sutured Over | 1 | 1 | 2 | 2 | 6 |
| Mesh | 2 | 1 | 0 | 0 | 3 |
|  | 2 | 1 | 3 | 1 | 7 |
| Average total Score |  |  |  |  | 5.0 |

[1]Seprafilm ® commercially available from Genzyme of Cambridge, MA.

As may be appreciated from a review of Table 1, with the exception of the negative control samples, all samples tested yielded good results with respect to inhibiting adhesion formation. However, it was observed that the CAP coated ORC/Polypropylene/PDS was most effective in preventing adhesion formation in the predictive rabbit sidewall model

EXAMPLE 5

Coating Substrate with Polymeric Coating Material Formulation

A 2 cm×4.5 cm piece of oxidized regenerated cellulose mesh substrate, which is commercially available from Ethicon, Inc. under the tradename, "INTERCEED," was coated with the polymeric coating material of Example 1 by pouring the polymeric coating material onto the substrate and evenly distributing the polymeric coating material with a blade under ambient conditions. The polymeric coating mixture was spread over the flip surface of the resulting substrate with a blade. The resulting dry weight gain of polymeric coating material on the substrate was, relative to the dry substrate alone, about 50 percent.

This procedure was repeated with 60 additional pieces of oxidized regenerated cellulose substrates.

EXAMPLE 6

Additional Adhesion Model Study Results

Additional adhesion evaluations at 14, 28 and 91 days of prototypes in the rabbit sidewall model are conducted. The purpose of such a study is to assess the extent and severity of adhesion formation of prototypes when compared to control in a rabbit sidewall model. A determination of the overall performance of each investigational test article is based on a comparison to the control with respect to the extent of adhesion formation and the severity of adhesion formation.

A test material is considered to be successful when it is shown to be superior to that of the negative control article.

The surgical procedures employed were as set forth in Example 4.

The adhesion extent scoring system employed was as set forth in Example 4.

Results are presented below, wherein each line represents a test preformed with a test article on a single independent animal.

TABLE 2

14 Day Necropsy Scores

| Test Article | Right Side Extent | Right Side Severity | Left Side Extent | Left Side Severity | Total Score |
|---|---|---|---|---|---|
| ORC/CAP Coated Mesh | 0 | 0 | 0 | 0 | 0 |
| of Example 5 Sutured | 0 | 0 | 0 | 0 | 0 |
| Over Defect | 0 | 0 | 0 | 0 | 0 |
|  | 0 | 0 | 0 | 0 | 0 |
| Average Total Score |  |  |  |  | 0.0 |
| Hyaluronic Acid/CMC | 0 | 0 | 0 | 0 | 0 |
| Film Sutured Over Mesh | 0 | 0 | 0 | 0 | 0 |
|  | 0 | 0 | 0 | 0 | 0 |
|  | 0 | 0 | 0 | 0 | 0 |
| Average Total Score |  |  |  |  | 0.0 |

[1]Seprafilm ® commercially available from Genzyme of Cambridge, MA.

TABLE 3

28 Day Necropsy Scores

| Text Article | Right Side Extent | Right Side Severity | Left side Extent | Left Side Severity | Total Score |
|---|---|---|---|---|---|
| ORC/CAP Coated Mesh | 0 | 0 | 0 | 0 | 0 |
| of Example 5 Sutured | 0 | 0 | 0 | 0 | 0 |
| Over Defect | 0 | 0 | 0 | 0 | 0 |
|  | 0 | 0 | 0 | 0 | 0 |
| Average Total Score |  |  |  |  | 0.0 |
| Hyaluronic Acid/CMC | 0 | 0 | 0 | 0 | 0 |
| Film Sutured Over Mesh | 0 | 0 | 1 | 1 | 2 |
|  | 0 | 0 | 0 | 0 | 0 |
|  | 0 | 0 | 0 | 0 | 0 |
| Average Total Score |  |  |  |  | 0.5 |

[1]Seprafilm ® commercially available from Genzyme of Cambridge, MA.

TABLE 4

91 Day Necropsy Scores

| Test Article | Right Side Extent | Right Side Severity | Left Side Extent | Left Side Severity | Total Score |
|---|---|---|---|---|---|
| ORC/CAP Coated Mesh of Example 5 Sutured Over Defect | 0 | 0 | 0 | 0 | 0 |
| | 0 | 0 | 0 | 0 | 0 |
| | 0 | 0 | 0 | 0 | 0 |
| | 0 | 0 | 0 | 0 | 0 |
| Average Total Score | | | | | 0.0 |
| Hyaluronic Acid/CMC Film Sutured Over Mesh | 0 | 0 | 0 | 0 | 0 |
| | 0 | 0 | 0 | 0 | 0 |
| | 0 | 0 | 1 | 3 | 4 |
| | 0 | 0 | 0 | 0 | 0 |
| Average Total Score | | | | | 1.0 |

[1]Seprafilm ® commercially available from Genzyme of Cambridge, MA.

As demonstrated above, the ORC/CAP coated mesh of Example 5 provided superior adhesion prevention performance when compared to the commercially available hyaluronic acid/CMC film.

EXAMPLE 7

Placement of Coated and Uncoated Substrates in Bloody Field

An uncoated sample of the substrate of Example 2 was placed in contact within a bloody surgical field. Almost immediately, the substrate was observed to wick-up the blood and turn black in color. For comparison, the procedure was repeated with the coated substrate of Example 3. The coated substrate was observed not to cause the matrix to wet or turn black after a period of greater than 20 minutes.

While the subject invention has been illustrated and described in detail in the drawings and foregoing description, the disclosed forms are illustrative and not restrictive in character. All changes and modifications that come within the scope of the invention are desired to be protected.

What is claimed is:

1. A method of inhibiting the formation of adhesions in a patient having undergone a surgical procedure, the method comprising the step of applying a surgical barrier to an area rendered susceptible to forming adhesions, the surgical barrier comprising: i) a wound-facing polymeric coating comprising cellulose acetate phthalate and hydroxypropylmethylcellulose; and ii) at least one flexible substrate in the form of a mesh, film, nonwoven fabric, or woven fabric and that is made from oxidized regenerated cellulose, the at least one flexible substrate having at least one exterior surface, wherein the polymeric coating is applied to the at least one flexible substrate to substantially cover the at least one exterior surface thereof.

2. The method of claim 1, wherein the the cellulose acetate phthalate and the hydroxypropylmethylcellulose are present in the polymeric coating in an amount of about 60:40 to about 40:60 by weight.

3. The method of claim 1, wherein said polymeric coating further comprises a non-enteric polymer and a plasticizer in an amount, based upon the total weight of the polymeric coating, from about 30 to about 60 percent of the cellulose acetate phthalate, from about 30 percent to about 60 percent of the non-enteric polymer, and from about 1 percent to about 35 percent of the plasticizer.

4. The method of claim 1, wherein the surgical barrier further comprises a non-enteric polymer selected from the group consisting of hydroxypropylcellulose, methylcellulose, hydroxyethylmethylcellulose, hydroxyethylcellulose, hydroxyethylethylcellulose, cellulose acetate, carboxymethyl cellulose sodium, cellulose butyrate, acetaldehyde dimethylcellulose acetate and derivatives, salts, copolymers and combinations thereof.

5. A method of repairing a perforation, the method comprising:
 a) closing the perforation with a surgical barrier in the form of a patch, the surgical barrier comprising: i) a polymeric coating comprising cellulose acetate phthalate and hydroxypropylmethylcellulose, an optional non-enteric polymer and an optional plasticizer; and ii) at least one flexible substrate in the form of a mesh, film, nonwoven fabric, or woven fabric and that is made from oxidized regenerated cellulose, the at least one flexible substrate having at least one exterior surface, wherein the polymeric coating is applied to the at least one flexible substrate to substantially cover the at least one exterior surface thereof.

* * * * *